US011000610B2

(12) United States Patent
Yang (10) Patent No.: US 11,000,610 B2
(45) Date of Patent: May 11, 2021

(54) PROCESS AND SYSTEM FOR IN-BASIN NEUTRALIZATION (71) Applicant: Ethicon, Inc., Somerville, NJ (US)

(72) Inventor: Sungwook Yang, Somerville, NJ (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 243 days.

(21) Appl. No.: 16/004,755

(22) Filed: Jun. 11, 2018

(65) Prior Publication Data
US 2019/0374667 A1 Dec. 12, 2019

(51) Int. Cl.
A61B 90/70 (2016.01)
A61L 2/18 (2006.01)
A62D 3/30 (2007.01)
C02F 1/00 (2006.01)
C02F 1/66 (2006.01)
C11D 11/00 (2006.01)
C11D 3/48 (2006.01)
C02F 103/00 (2006.01)

(52) U.S. Cl.
CPC ............... *A61L 2/186* (2013.01); *A62D 3/30* (2013.01); *C02F 1/66* (2013.01); *C11D 3/48* (2013.01); *C11D 11/0064* (2013.01); *A61B 90/70* (2016.02); *A61L 2202/122* (2013.01); *A61L 2202/14* (2013.01); *A61L 2202/24* (2013.01); *A62D 2203/10* (2013.01); *C02F 1/008* (2013.01); *C02F 2103/003* (2013.01); *C02F 2303/18* (2013.01)

(58) Field of Classification Search
CPC . A61B 90/70; A61L 2/18; A61L 2/186; A61L 2202/122; A61L 2202/14; A61L 2202/24; A62D 3/30; A62D 2203/10; C02F 1/008; C02F 1/66; C02F 2103/003; C02F 2303/18; C11D 3/48; C11D 11/0064
See application file for complete search history.

(56) References Cited

U.S. PATENT DOCUMENTS 4,804,478 A * 2/1989 Tamir ...................... C02F 1/78
210/752
6,399,850 B1 6/2002 Chen et al.
(Continued)

OTHER PUBLICATIONS

International Search Report and Written Opinion for PCT/IB2019/000752 dated Dec. 4, 2019.

*Primary Examiner* — Lucas A Stelling
(74) *Attorney, Agent, or Firm* — K&L Gates LLP (57) ABSTRACT A method and system for in-basin neutralization is provided. More specifically, neutralizer is added to a basin in excess of an amount of neutralizer suitable to neutralize a treatment solution in a reservoir in fluid communication with the basin. A first portion of the treatment solution is added to the basin and is contacted with the first portion of the treatment solution to form a secondary solution. The first portion of the treatment solution is neutralized with the neutralizer. A first portion of the secondary solution is removed from the basin. A second portion of the treatment solution is added to the basin. The second portion of the treatment solution is contacted with a second portion of the secondary solution remaining the basin to form a tertiary solution. The second portion of the treatment solution is neutralized with neutralizer in the second portion of the secondary solution.

19 Claims, 10 Drawing Sheets

(56) References Cited

U.S. PATENT DOCUMENTS

| | | | |
|---|---|---|---|
| 6,531,634 B1 | 3/2003 | Zhu | |
| 7,467,890 B2 | 12/2008 | Patzek, IV | |
| 7,662,294 B1 * | 2/2010 | Cox, Jr. | A62D 3/00 |
| | | | 210/759 |
| 2012/0091070 A1 * | 4/2012 | Sjauta | C02F 1/003 |
| | | | 210/764 |
| 2016/0318780 A9 * | 11/2016 | Bain | C02F 1/78 |
| 2017/0332892 A1 | 11/2017 | Yang et al. | |

* cited by examiner

PROCESS AND SYSTEM FOR IN-BASIN NEUTRALIZATION

FIELD OF THE INVENTION

The present disclosure relates to systems and methods for in-basin neutralization of a treatment solution.

BACKGROUND

The medical field employs various devices for medical procedures. One such device is an endoscope that examines the interior of a hollow organ or cavity of the body. A critical aspect of all medical procedures and devices is the prevention of cross-contamination and the spread of disease. In this regard, treatment solutions such as, for example, cleaning solutions, disinfectant solutions, and/or sterilant solutions are used on medical devices and facility surfaces. These solutions, by their nature, include relatively harsh constituents in order to effectively clean, disinfect, and/or sterilize devices and/or surfaces. Disposing of the treatment solution after use can be inconvenient for an operator and/or expose the operator to the treatment solution.

Improvement in the health and safety conditions of the environment, operators, and patients are an important focus of the medical field. In this regard, efforts have been made to limit exposure of operators and hospital personnel to treatment solutions.

SUMMARY

In one aspect, the present disclosure provides a method for in-basin neutralization in a chamber comprising a basin in fluid communication with a reservoir. More specifically, neutralizer is added to the basin in excess of an amount of neutralizer suitable to neutralize a treatment solution in the reservoir. A first portion of the treatment solution is added to the basin. The neutralizer is contacted with the first portion of the treatment solution to form a secondary solution and the first portion of the treatment solution is neutralized with the neutralizer. A first portion of the secondary solution is removed from the basin and a second portion of the secondary solution remains in the basin. A second portion of the treatment solution is added to the basin. The second portion of the treatment solution is contacted with the second portion of the secondary solution to form a tertiary solution and the second portion of the treatment solution is neutralized with neutralizer in the second portion of the secondary solution.

In another aspect, the present disclosure provides a method for in-basin neutralization in a chamber comprising a basin in fluid communication with a reservoir. More specifically, neutralizer is added to the basin in excess of an amount of neutralizer suitable to neutralize a disinfectant solution in the reservoir. The basin has a first solution capacity and the reservoir has a second solution capacity larger than the first solution capacity. A first portion of the disinfectant solution is added to the basin. The neutralizer is contacted with the first portion of the disinfectant solution to form a secondary solution and the first portion of the disinfectant solution is neutralized with the neutralizer. A first portion of the secondary solution is removed from the basin and a second portion of the secondary solution remains in the basin. The second portion of the secondary solution comprises an amount of neutralizer suitable to neutralize a second portion of the disinfectant solution. The second portion of the disinfectant solution is added to the basin. The second portion of the disinfectant solution is contacted with the second portion of the secondary solution to form a tertiary solution and the second portion of the disinfectant solution is neutralized with neutralizer in the second portion of the secondary solution.

In another aspect, a system is provided for in-basin neutralization. The system comprises a reservoir and a basin in fluid communication with the reservoir. The reservoir comprises a disinfectant solution. The basin is suitable to receive disinfectant solution from the reservoir. The basin has a first solution capacity and the reservoir has a second solution capacity larger than the first solution capacity. The basin comprises a neutralizing solution suitable to neutralize the disinfectant solution in the reservoir. A mole ratio of active group in the neutralizer to active group in the disinfectant solution is greater than 1.3:1.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Any references herein to "various examples," "some examples," "one example," "an example", similar references to "aspects," or the like, means that a particular feature, structure, or characteristic described in connection with the example is included in at least one example. Thus, appearances of the phrases "in various examples," "in some examples," "in one example", "in an example", similar references to "aspects," or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited.

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

As used herein "active group" is meant to mean the chemical that is participating in the neutralization reaction.

As used herein when referring to the presence of a particular constituent "substantially free" is meant to mean at least 90% free of that constituent, and in some examples at least 95%, 96%, 97%, and 98% free, in other examples at least 99% free, in other examples at least 99.9% free, in other examples at least 99.99% free, in some examples at least 99.999% free, and in other examples at least 99.9999% free of that constituent.

A treatment solution process may be at least one of a cleaning solution, a disinfectant solution, and a sterilant solution. A treatment process may be at least one of a cleaning process, a disinfection process, and a sterilization process. A cleaning process may be a process which reduces and/or eliminates a dirt, a dust, a particle, and the like utilizing a cleaning solution. A disinfection process may be a type of a cleaning process which reduces and/or eliminates bacteria and/or other forms of living organisms utilizing a disinfectant solution. A sterilization process may be a type of disinfection process that reduces and/or eliminates bacteria and/or other forms of living organisms that results in a sterilized object being substantially free from bacteria and/or other forms of living organisms utilizing a sterilant.

In multi-use treatment systems, a larger quantity of treatment solution can be kept in a reservoir than required for a treatment process cycle to account for any loses of treatment solution during the treatment process cycle. Typically, disposing of the treatment solution from multi-use treatment systems can require removing all the treatment solution from the multi-use treatment system and placing the treatment solution in a secondary container outside of the multi-use treatment systems. The treatment solution can be neutralized in the secondary container by adding neutralizer to the secondary container. Thereafter, the neutralized solution can be disposed of by, for example, emptying the neutralized solution in a waste drain. This process can be time consuming and expose an operator of the multi-use treatment system to the relatively harsh effects of the treatment solution. Thus, a method and a system are provided for in-basin neutralization that can limit operator exposure to the treatment solution, decrease the time spent neutralizing treatment solution, and/or create an automated procedure for neutralization of the treatment solution.

According to the present disclosure, neutralizer may be added to the basin in excess of an amount of neutralizer suitable to neutralize a treatment solution in a reservoir in fluid communication with the basin. A first portion of the treatment solution may be added to the basin. The neutralizer may be contacted with the first portion of the treatment solution to form a secondary solution in the basin and the first portion of the treatment solution may be neutralized with the neutralizer. A first portion of the secondary solution may be removed from the basin wherein a second portion of the secondary solution remains in the basin. A second portion of the treatment solution may be added to the basin. The second portion of the treatment solution may be contacted with the second portion of the secondary solution to form a tertiary solution in the basin, and the second portion of the treatment solution may be neutralized with neutralizer in the second portion of the secondary solution.

Figure 1:
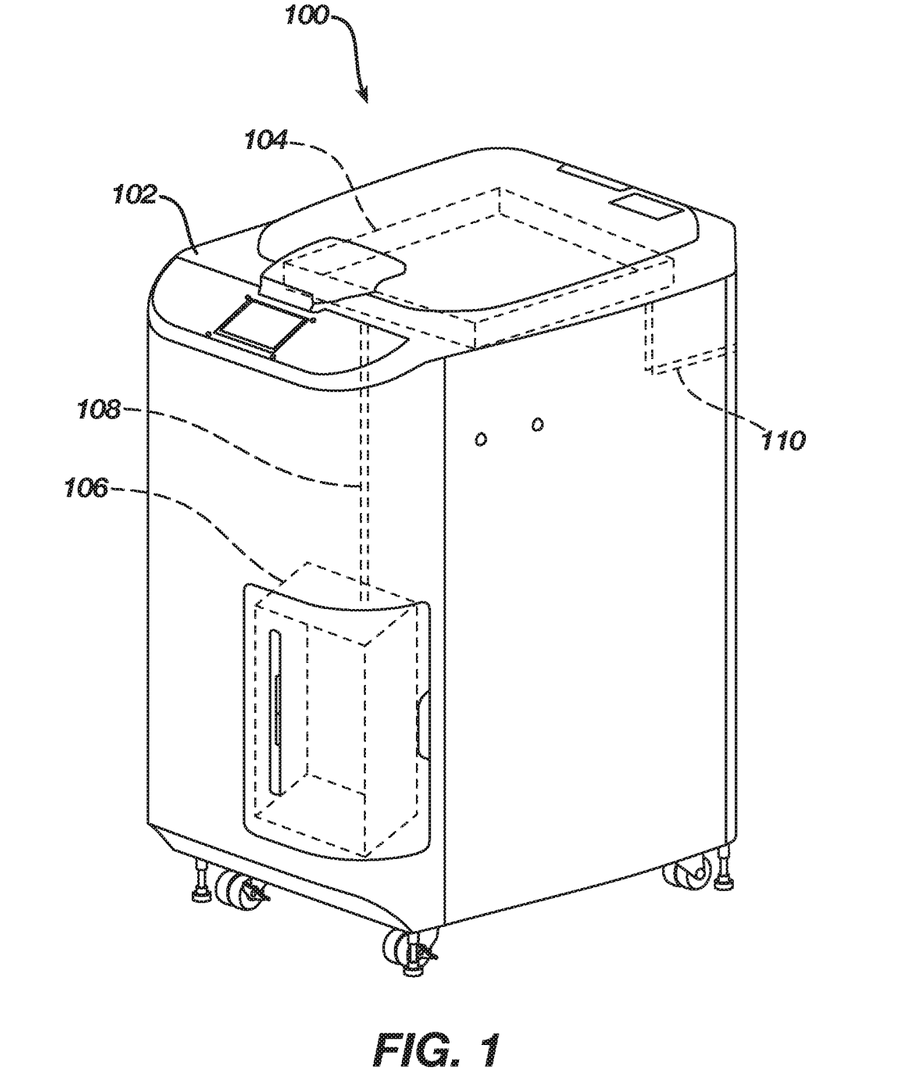
FIG. 1 is a depiction of a system for in-basin neutralization of a treatment solution according to the present disclosure.
Figure 2:
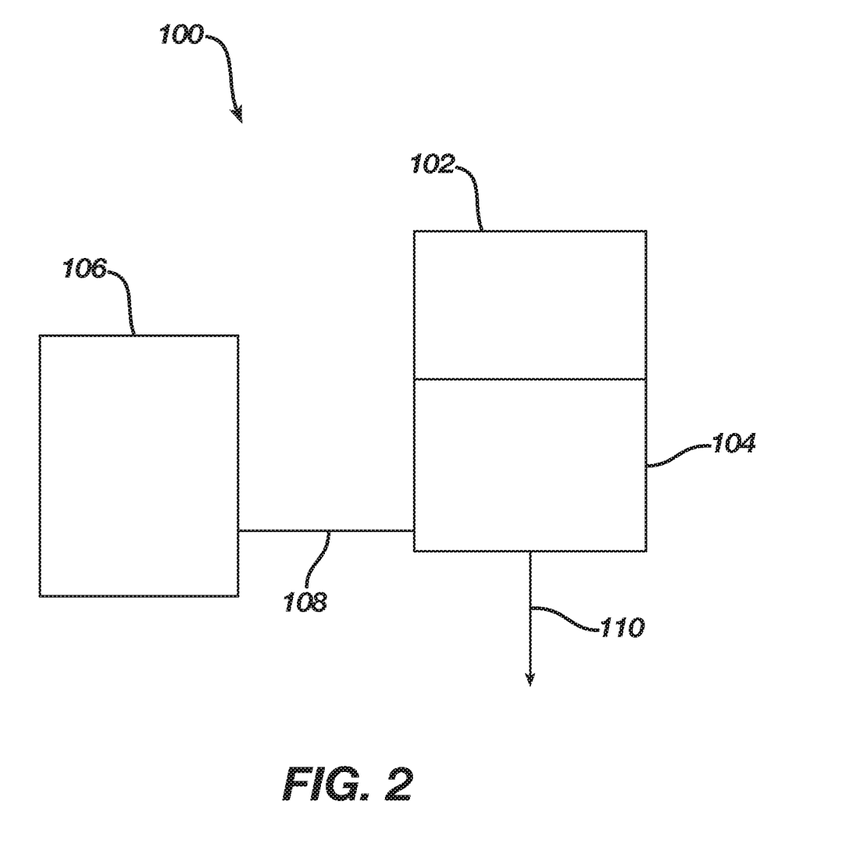
FIG. 2 is a schematic front view of a system for in-basin neutralization of a treatment solution according to the present disclosure.

FIGS. 1 and 2 illustrate a system 100 for in-basin neutralization of a treatment solution according to the present disclosure. As illustrated, the system 100 can comprise a chamber 102 including a basin 104 in fluid communication with a reservoir 106. The chamber 102 may be suitable to receive a medical device (not shown), and can be suitable to perform a treatment process on the medical device. In various examples, the chamber 102 can comprise at least one of a heating element, a pump, a wash arm, a spray nozzle, a tube, and other devices known to one of ordinary skill in the art. In various examples, the chamber 102 can be at least one of a cleaning chamber, a disinfection chamber, and a sterilization chamber. In certain examples, the medical device can comprise an endoscope. In various examples, the system 100 can comprise an endoscope re-processor.

The reservoir 106 can be suitable to receive a treatment solution and can store the treatment solution until the treatment solution can be output into the basin 104. The basin 104 can be in fluid communication with the reservoir 106 via a treatment line 108. The treatment line 108 can be suitable to receive the treatment solution from the reservoir 106 and transport the treatment solution to the basin 104. In various examples, the treatment line 108 can include at least one of a tube, a valve, and a pump. The treatment line 108 can control the amount of treatment solution provided to the basin 104. For example, the treatment solution can be metered into the basin 104 by the treatment line 108 until a select amount of treatment solution has been provided to the basin 104. The basin 104 can be suitable to receive treatment solution from the reservoir 106 via the treatment line 108.

The treatment solution can comprise at least one of a cleaning solution, a disinfectant solution, and a sterilant solution. In certain examples, the treatment solution comprises a disinfectant solution including a disinfectant. The disinfectant can comprise at least one of an alcohol, an aldehyde, a quaternary ammonium compound, an oxidizer, and an antimicrobial metal solution. In certain examples, the disinfectant can comprise ortho-phthalaldehyde (OPA). In various examples, the disinfectant solution can comprises AERO-OPA™ available from Advanced Sterilization Products, A Division of Ethicon, Inc., a Johnson & Johnson company located in Irvine, Calif.

The basin 104 can have a basin solution capacity and the reservoir 106 can have a reservoir solution capacity. In various examples, the reservoir solution capacity can be larger than the basin solution capacity. For example, the reservoir solution capacity can be at least 10% larger than the basin solution capacity such as, for example, at least 20% larger than the basin solution capacity, at least 30% larger than the basin solution capacity, at least 50% larger than the basin solution capacity, or at least 100% larger than the basin solution capacity. In certain examples, the reservoir solution capacity may be 10% to 200% larger than the basin solution capacity such as, for example, 10% to 100% larger and in other aspects is 20% to 100% larger than the basin solution capacity. In various examples, the reservoir has a solution capacity from 1 liter (L) to 50 L such as, for example, 2 L to 30 L, 10 L to 15 L, or 12 L.

If the treatment solution has a characteristic deemed improper for disposal into the environment (e.g., disposal down a drain, transport to a wastewater treatment facility, etc.) according to local law, the treatment solution may require special handling and/or require neutralization. For example, according to California Code 22 CCR § 66261.24, a waste may require special handling and/or require neutralization prior to disposal if "it has an acute aquatic 96-hour LC50 less than 500 milligrams per liter when measured in soft water (total hardness 40 to 48 milligrams per liter of calcium carbonate) with fathead minnows (*Pimephales promelas*), rainbow trout (*Salmo gairdneri*) or golden shiners (*Notemigonus crysoleucas*) according to procedures described in Part 800 of the "Standard Methods for the Examination of Water and Wastewater (16th Edition)," American Public Health Association, 1985 and "Static Acute Bioassay Procedures for Hazardous Waste Samples," California Department of Fish and Game, Water Pollution Control Laboratory, revised November 1988." In order to neutralize the treatment solution, a neutralizer can be added to the basin 104 such that special handling may not be required for the treatment solution and/or the treatment solution can be disposed of into the environment according to local law. In various examples, the neutralizer can increase the $LC_{50}$ of the treatment solution such that the treatment solution can have an $LC_{50}$ of greater than 500 mg/L.

The addition of the neutralizer to the basin 104 can be automated such as, for example, by pumping the neutralizer into the basin 104, or by the manual addition of neutralizer to the basin 104. The neutralizer can be a solution of neutralizer or solid concentrated neutralizer. The neutralizer can comprise at least one of an amino acid, ammonia, sodium hydroxide, hydrogen peroxide, sodium hypochlorite, and sodium bisulfite. The amino acid can include at least one of alanine, proline, amino-caproic acid, phenylalanine, tryptophan, methionine, glycine, serine, cycteine, tyrosine, lysine, arginine, glutamine, aspartic acid, glutamic acid, and histidine. In various examples, the amino acid can comprise glycine. In certain examples, the neutralizer can comprise a 6% glycine by weight solution. In various examples, the neutralizer can comprise KemSafe™ Solution Neutralizer Catalog #9074 available from Kem Medical Products Corp., located in Farmingdale, N.Y.

The neutralizer can be added to the basin 104 in excess of an amount of neutralizer suitable to neutralize the treatment solution in the reservoir 106. The amount of neutralizer suitable to neutralize the treatment solution in the reservoir 106 can be a mole ratio of active group in the neutralizer to active group in the treatment solution of at least 1. For example, the neutralizer can be added to the basin 104 in a mole ratio of active group in the neutralizer to active group in the treatment solution of greater than 1.3:1 such as, for example, greater than 1.5:1, greater than 2:1, or greater than 3:1. In certain examples, the neutralizer can be added to the basin in a mole ratio of active group in the neutralizer to active group in the treatment solution in a range of 1.1:1 to 10:1 such as, for example, 1.2:1 to 5:1, 1.3:1 to 3:1, or 1.3:1 to 1.5:1.

Neutralization of the treatment solution can include forming an adduct between the treatment solution and the neutralizer. For example, when the treatment solution comprises an aldehyde (e.g., OPA) and the neutralizer comprises an amino acid (e.g., glycine), the reaction of the neutralizer with the treatment solution can proceed as shown in Scheme 1.

Scheme 1

As illustrated in Scheme 1, an amine group of the amino acid can react with the aldehyde to form an adduct. The amine group can deactivate the aldehyde by forming the adduct which is more suitable for handling and/or disposal than the aldehyde alone. In certain examples, the adduct is an N-substituted adduct. In various examples, when using OPA and glycine, the formed adduct can be black in color which can indicate the solution has been neutralized.

Neutralization of the treatment solution can occur in at least two phases. For example, in a first phase, excess neutralizer can be added to the basin 104 and a first portion of the treatment solution can be added to the basin 104 from the reservoir 106 in the amounts and ratios provided herein. The first portion of the treatment solution can be less than the reservoir solution capacity. In various examples, the first portion of the treatment solution is from 5% to 95% of the reservoir solution capacity such as, for example, 10% to 90% or 65% to 80%. A second portion of the treatment solution can remain in the reservoir 106 after removal of the first portion of treatment solution from the reservoir 106.

In the first phase, the neutralizer can be contacted with the first portion of the treatment solution in the basin 104 to form a secondary solution and the first portion of the treatment solution can be neutralized by the neutralizer. The contacting may include at least one of heating, agitating, and circulating. The secondary solution can comprise formed adduct and neutralizer suitable to neutralize the second portion of the treatment solution in the reservoir 106. In various examples, the secondary solution can comprise at least one of treatment solution and water. In various examples, the secondary solution can be substantially free of treatment solution. In certain examples, the neutralizer is only added during the first phase.

A first portion of the secondary solution can be removed from the basin 104 via a drain line 110. The drain line 110 can be suitable to receive the secondary solution from the basin 104 and can transport the secondary solution out of the basin 104. A second portion of the secondary solution can remain in the basin 104 after the removal of the first portion of the secondary solution. The amount of the first portion of the secondary solution removed can be controlled so that the second portion of the secondary solution contains an amount of active neutralizer suitable to neutralize the remaining treatment solution in the reservoir. In various examples, the second portion of the secondary solution is from 5% to 95% of the basin solution capacity such as, for example, 10% to 90% or 5% to 40%.

In a second phase, the second portion of the treatment solution can be added to the basin 104 from the reservoir 106 and can be added to the second portion of the secondary solution in the basin 104. In the second phase, the active neutralizer remaining in the secondary solution can be contacted with the second portion of the treatment solution in the basin to form a tertiary solution and the second portion of the treatment solution can be neutralized by the neutralizer. The contacting may include at least one of heating, agitating, and circulating. In various examples, the amount of tertiary solution can be equal to or less than the basin solution capacity. The tertiary solution can comprise formed adduct. In various examples, the tertiary solution can comprise at least one of neutralizer, treatment solution, and water. In various examples, the tertiary solution is substantially free of treatment solution. In certain examples, no additional neutralizer is added during the second phase.

The number of phases to neutralize the treatment solution should not be considered limiting. For example, the treatment solution in the reservoir can be neutralized in the basin 104 in two or more phases, such as at least three phases. In various examples, the second portion of the treatment solution is all of the remaining treatment solution in the reservoir 106 after removal of the first portion of treatment solution. In various examples, the second portion of the treatment solution is less than all of the remaining treatment solution in the reservoir 106. In certain examples, no additional neutralizer is added after the first phase.

In certain examples, the treatment solution in the reservoir 106 can be neutralized in at least three phases. For example, in a third phase, a first portion of the tertiary solution can be removed from the basin 104 via the drain line 110. A second portion of the tertiary solution can remain in the basin 104 after the removal of the first portion of the tertiary solution. The second portion of the tertiary solution contains an amount of active neutralizer suitable to neutralize the remaining treatment solution in the reservoir.

A third portion of the treatment solution can be added to the basin 104 from the reservoir 106 and can be added to the second portion of the tertiary solution in the basin 104. The active neutralizer remaining in the second portion of the tertiary solution can be contacted with the third portion of the treatment solution in the basin 104 to form a quaternary solution and the third portion of the treatment solution can be neutralized by the neutralizer. The contacting may include at least one of heating, circulating, and agitating. In various examples, the amount of the quaternary solution can be equal to or less than the basin solution capacity. The quaternary solution can comprise formed adduct. In various examples, the quaternary solution can comprise at least one of neutralizer, treatment solution, and water. In various examples, the quaternary solution is substantially free of treatment solution. In certain examples, no additional neutralizer is added during the third phase.

Additional phases of neutralization may be added as needed to neutralize the treatment solution in the reservoir 106 such that the treatment solution can be more suitable for handling and/or disposal. The secondary, tertiary, and/or quaternary solutions, and/or additional solutions of the neutralization process that are removed from the basin can have an $LC_{50}$ greater than 500 mg/L such as, for example, greater than 600 mg/L, greater than 700 mg/L, greater than 800 mg/L, greater than 1000 mg/L, or greater than 2000 mg/L. In various examples, the secondary, tertiary, and/or quaternary solutions, and/or additional solutions of the neutralization process that are removed from the basin contain less than 0.1% by weight of the secondary solution of active treatment solution (e.g., treatment solution containing an un-neutralized active group) such as, for example, less than 0.01% by weight of the secondary solution, and, in certain examples, substantially 0% by weight of the secondary solution.

The secondary, tertiary, and/or quaternary solutions, and/ or additional solutions can be removed from the basin 104 via the drain line 110 and can be disposed of. At least one of the reservoir 106 and the basin 104 can be rinsed with an aqueous solution after removing the tertiary solution. In various examples, the reservoir 106 and the basin 104 can each be rinsed with an aqueous solution multiple times, and in some examples is rinsed at least two times, in other examples at least three times, and in other examples three times. The aqueous solution can comprise water.

In various examples, the first phase and second phase of processing can have a duration of 1 minute to 20 minutes such as, for example, 2 minutes to 10 minutes, and in other examples 2 to 5 minutes. In certain examples, the rinse stage can have a duration of 1 minute to 30 minutes, such as, for example, 1 minute to 20 minutes or 1 to 10 minutes. In various examples, the duration to neutralize the treatment solution in the reservoir 106 can be from 6 minutes to 1 hour such as, for example, 12 minutes to 30 minutes or 20 minutes to 25 minutes.

The amount of neutralizer that can be added in the first phase can be represented by Equation 1.

$$\frac{Ratio_M * TS}{SS_R * \ldots N_R} = \text{Amount of Neutralizer to Add in First Phase} \quad \text{Equation 1}$$

wherein:

$Ratio_M$ is the desired mole ratio of active group of neutralizer to active group of treatment solution;

TS is the amount of treatment solution in the reservoir;

$SS_R$ is the percent of secondary solution to be removed; and $N_R$ is the product of the percent(s) of neutralized solution (s) to be removed in each subsequent phase of neutralization. For a two-phase neutralization the variable $N_R$ equals 1.

Figure 3A:
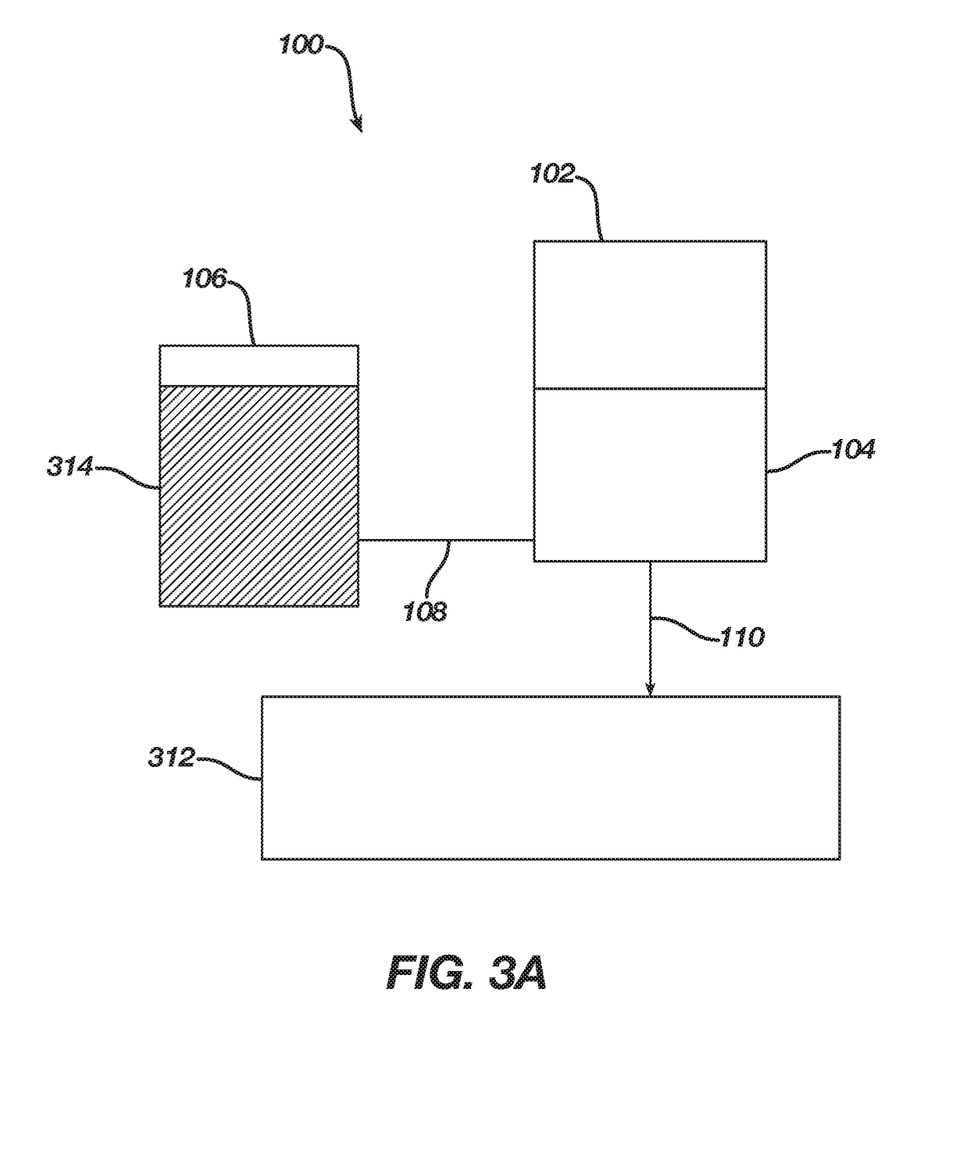
FIG. 3A is a schematic front view of a system for in-basin neutralization in a first stage of neutralization according to the present disclosure.

FIGS. 3A-H are schematic front views of a system 100 for in-basin neutralization in various stages of neutralization according to the present disclosure. FIG. 3A illustrates the system 100 in a first stage of neutralization. The system 100 includes the chamber 102 which comprises the basin 104 in fluid communication with the reservoir 106 via treatment line 108 and a disposal system 312 via drain line 110. The reservoir 106 can be filled with treatment solution 314.

Figure 3B:
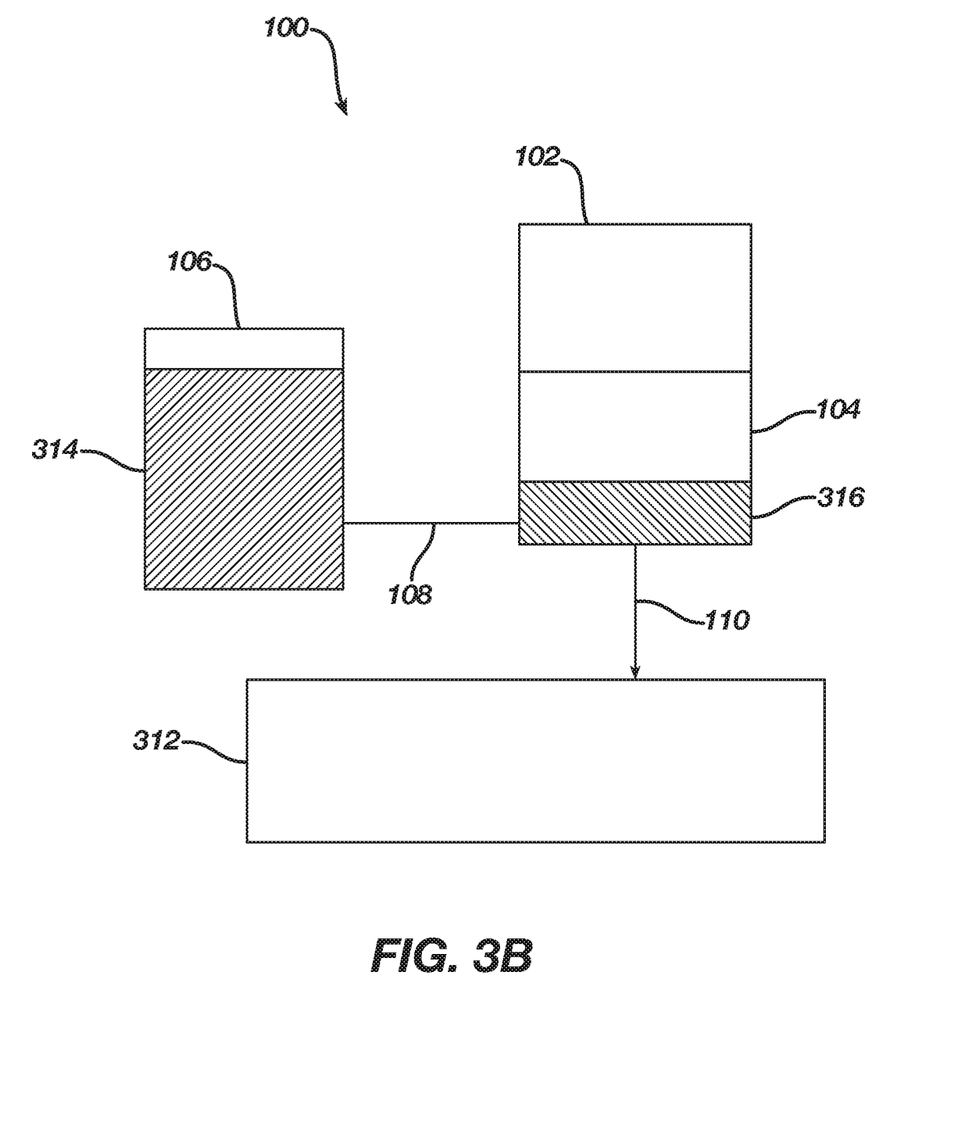
FIG. 3B is a schematic front view of the system for in-basin neutralization of FIG. 3A in a second stage of neutralization according to the present disclosure.
Figure 3C:
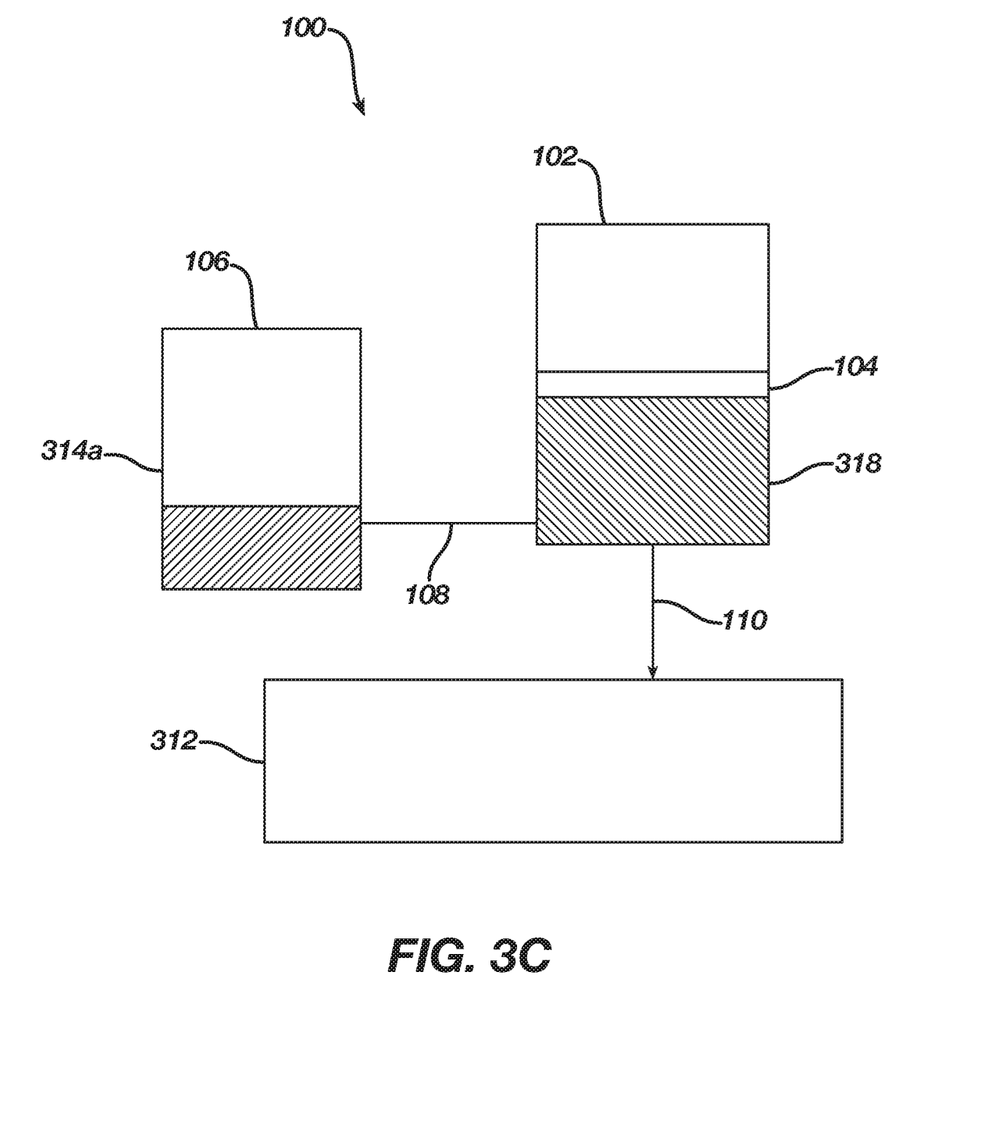
FIG. 3C is a schematic front view of the system for in-basin neutralization of FIG. 3A in a third stage of neutralization according to the present disclosure.
Figure 3D:
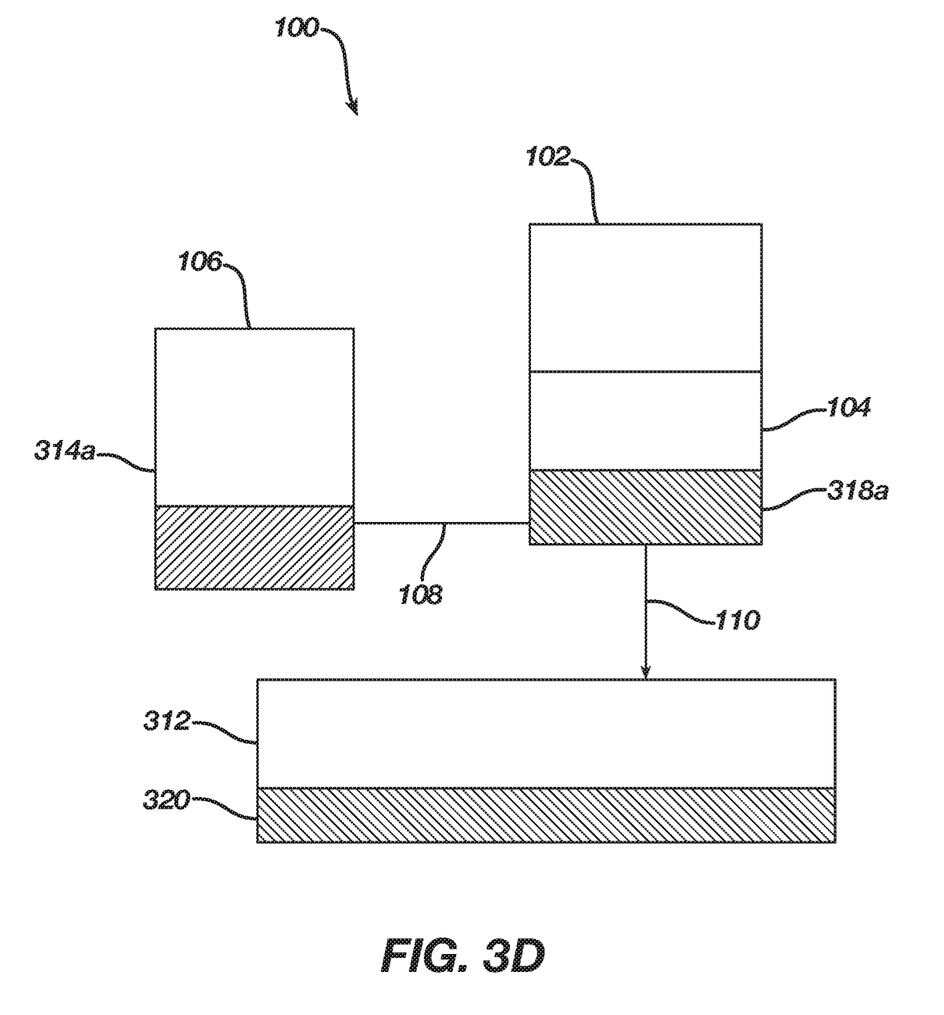
FIG. 3D is a schematic front view of the system for in-basin neutralization of FIG. 3A in a fourth stage of neutralization according to the present disclosure.

FIG. 3B illustrates a second stage of neutralization where a neutralizer 316 has been added to the basin 104 in excess of an amount of neutralizer 316 suitable to neutralize the treatment solution 314 in the reservoir 106. A first portion of treatment solution 314 can be added to the basin 104 and the first portion of the treatment solution 314 can be contacted with the neutralizer 316 to form a secondary solution 318 as illustrated in a third stage of neutralization in FIG. 3C. In various examples, the neutralizer 316 reacts with the first portion of the treatment solution 314 to form an adduct between the first portion of the treatment solution 314 and the neutralizer 316. In various examples, the first portion of the treatment solution 314 can be added to the basin 104 prior to adding the neutralizer 316 to the basin 104. FIG. 3D illustrates a fourth stage of neutralization where a first portion of the secondary solution 318 is removed from the basin 104 via the drain line 110 and provided to the disposal system 312 as a waste 320. A second portion 318a of the secondary solution 318 remains in the basin 104. The second portion 318a of the secondary solution 318 comprises an amount of neutralizer 316 suitable to neutralize the remaining treatment solution 314a in the reservoir 106. In various examples, FIGS. 3B-D can be a first phase of neutralization.

Figure 3E:
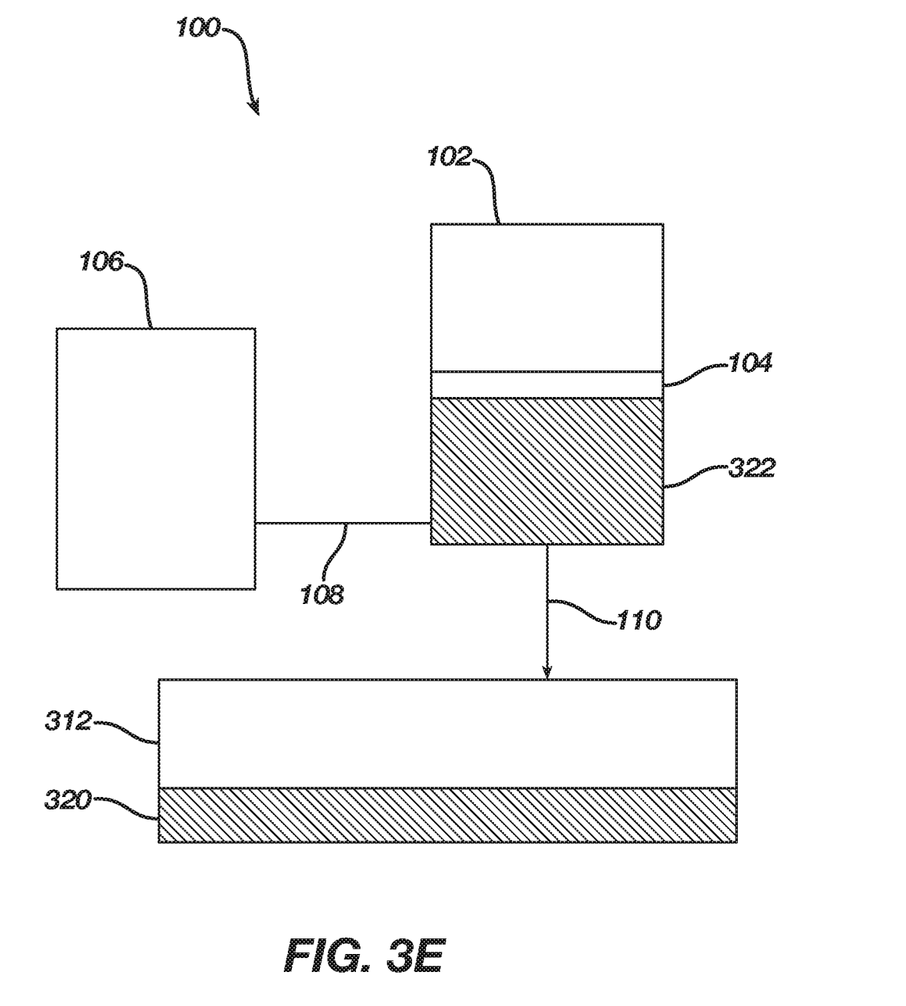
FIG. 3E is a schematic front view of the system for in-basin neutralization of FIG. 3A in a fifth stage of neutralization according to the present disclosure.

FIG. 3E illustrates a fifth stage of neutralization where a second portion of the treatment solution 314 can be added to the basin 104 and the second portion of the treatment solution 314 can be contacted with the second portion 318a of the secondary solution 318 to form a tertiary solution 322. In various examples, the neutralizer 316 in the secondary solution 318 can react with the second portion of the treatment solution 314 to form an adduct between the second portion of the treatment solution 314 and the neutralizer 316 in the secondary solution 318. In various examples, the second portion of the treatment solution 314 can comprise the remaining treatment solution 314a in the reservoir 106. In other examples, the second portion of the treatment solution 314 can be less than the remaining treatment solution 314a in the reservoir 106. The fourth stage in FIG. 3D and the fifth stage in FIG. 3E may be repeated as needed to neutralize the remaining treatment solution in the reservoir 106. In various examples, FIG. 3E can be a second phase of neutralization.

Figure 3F:
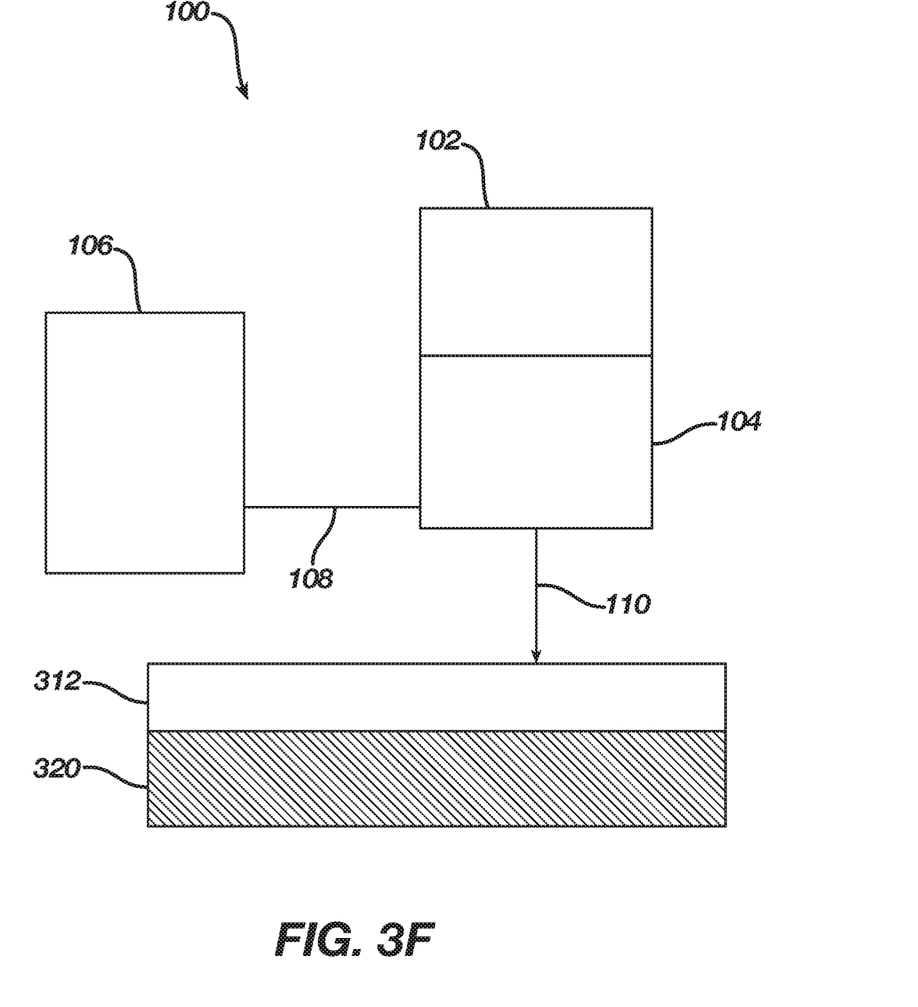
FIG. 3F is a schematic front view of the system for in-basin neutralization of FIG. 3A in a sixth stage of neutralization according to the present disclosure.
Figure 3G:
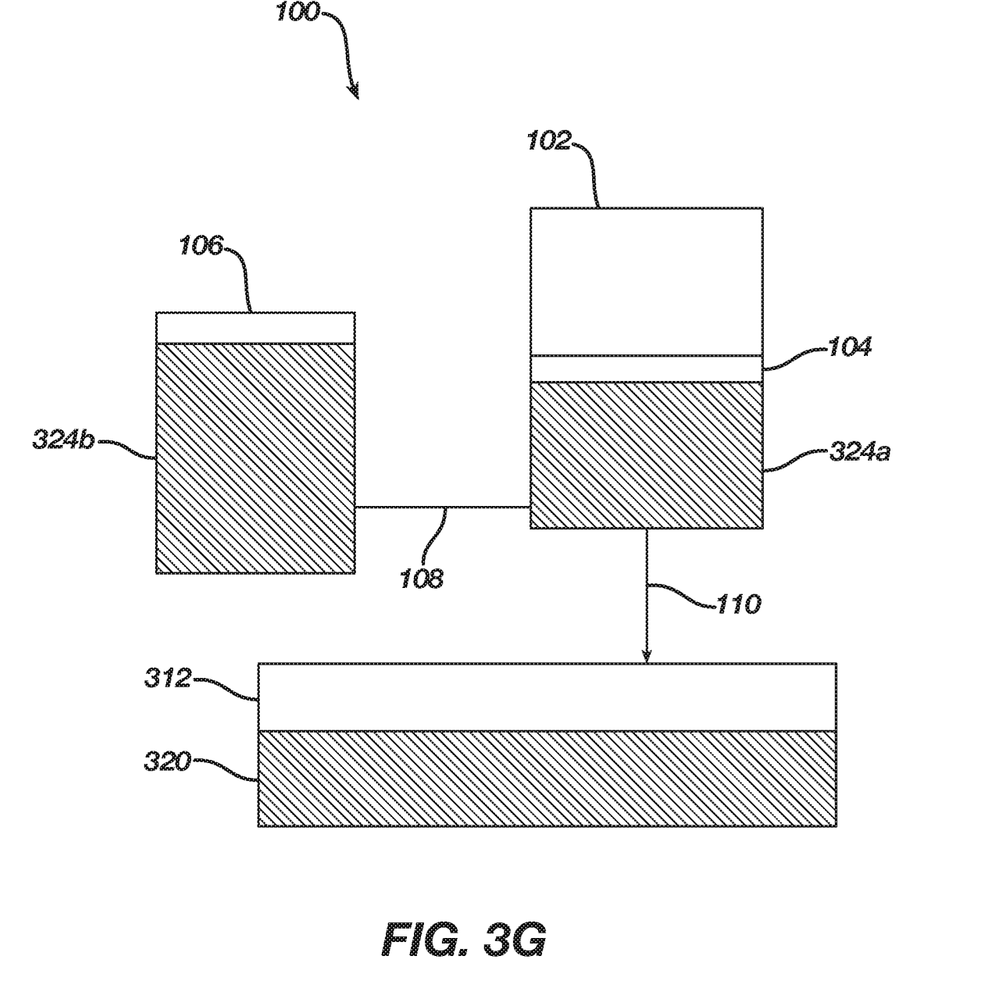
FIG. 3G is a schematic front view of the system for in-basin neutralization of FIG. 3A in a seventh stage of neutralization according to the present disclosure.
Figure 3H:
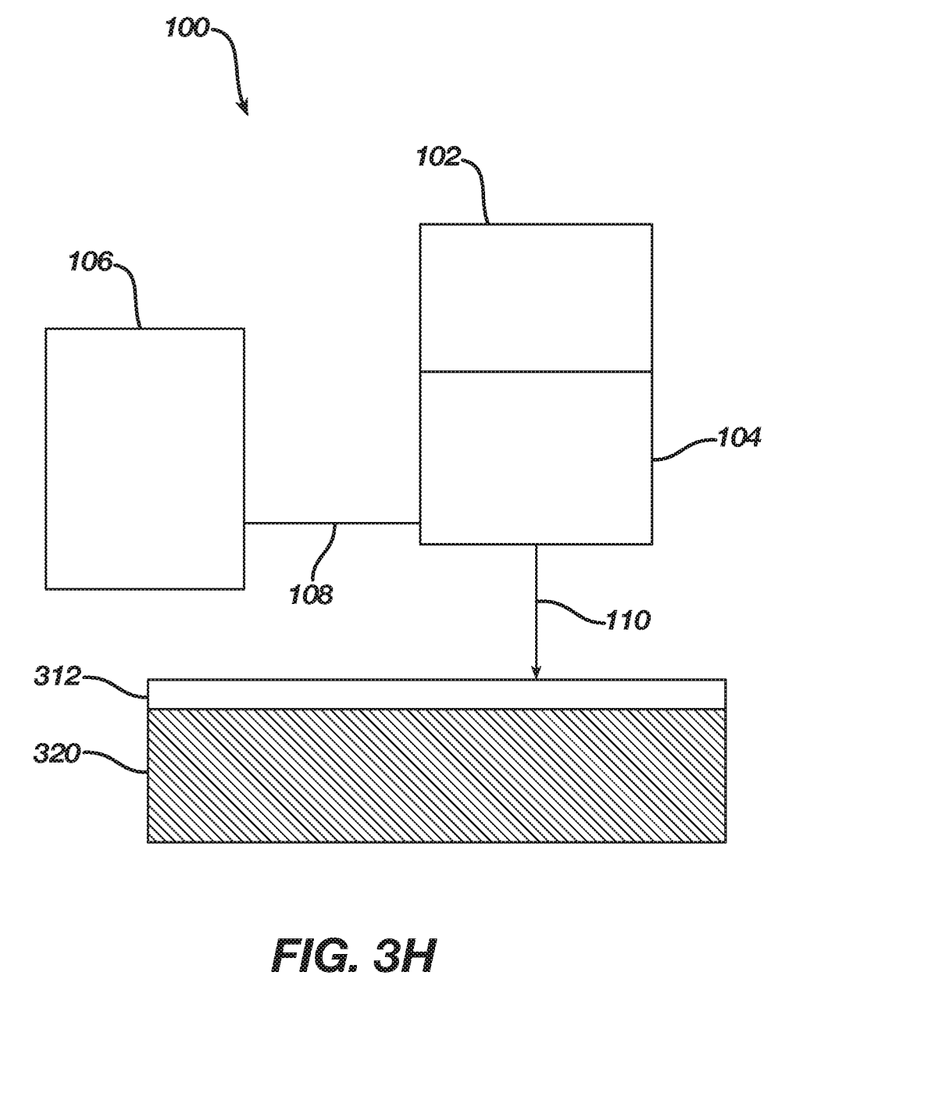
FIG. 3H is a schematic front view of the system for in-basin neutralization of FIG. 3A in an eighth stage of neutralization according to the present disclosure.

In various examples, as illustrated in a sixth stage in FIG. 3F, the tertiary solution 322 has been removed from the basin 104 via drain line 110 and provided to the disposal system 312 as waste 320. FIG. 3G illustrates a seventh stage where the basin 104 can be filled with an aqueous solution 324a to rinse the basin 104 and remove residual neutralizer 316, treatment solution 314, secondary solution 318, tertiary solution 322, and/or additional solutions of the neutralization process that are removed from the basin 104. In various examples, in the seventh stage, the reservoir 106 can be filled with an aqueous solution 324b. The aqueous solution 324a, 324b can be removed from the system 100 via drain line 110 and can be provided to the disposal system 312 as waste 320 as illustrated in an eighth stage in FIG. 3H. The seventh stage in FIG. 3G and the eighth stage in FIG. 3H can be repeated as needed to remove residual treatment solution 314 from the reservoir 106 and/or residual neutralizer 316, treatment solution 314, secondary solution 318, tertiary solution 322, and/or additional solutions of the neutralization process that are removed from the basin 104.

According to the present disclosure, in-basin neutralization can limit cross-contamination in the reservoir since neutralizer may not have to be added to the reservoir. If neutralizer was added directly to the reservoir, residual neutralizer may be left after the neutralization process, which can degrade a subsequent treatment solution added to the reservoir. The degraded treatment solution may not be as effective or properly clean, disinfect, and/or sanitize in a treatment process.

In various examples, the method and system according to the present disclosure can neutralize the treatment solution in the reservoir with only a single addition of neutralizer to the basin. The single addition of neutralizer can improve the conditions of the solution for operator exposure and/or decrease the time spent neutralizing treatment solution.

EXAMPLES

A 12 L capacity reservoir was prepared in fluid communication with a 9 L basin of an endoscope re-processor. The reservoir was filled with 12 L of AERO-OPA™ available from Advanced Sterilization Products, a Division of Ethicon, Inc., a Johnson & Johnson company, located in Irvine, Calif. (0.55% OPA by weight). The 12 L of AERO-OPA™ in the reservoir was neutralized in two phases. The duration of each phase was 5 minutes and the total neutralization time was 10 minutes.

In the first phase, the basin was filled with 2 L of KemSafe™ Solution Neutralizer Catalog #9074 available from Kem Medical Products Corp., located in Farmingdale, N.Y. (6% glycine by weight). 7 L of the AERO-OPA™ was provided to the basin from the reservoir. The 7 L of AERO-OPA™ was contacted with the 2 L of neutralizer to form a secondary solution. 5 L of the secondary solution was removed from the basin and 4 L of the secondary solution remained in the basin.

In the second phase, the remaining 5 L of AERO-OPA™ was provided to the basin from the reservoir and contacted with the 4 L of secondary solution remaining in the basin to form a tertiary solution. The tertiary solution was removed from the basin and the basin was rinsed with 9 L of water.

The secondary and tertiary solution were combined and tested to determine the $LC_{50}$ of the combined solution. The test was performed according to the "Standard Methods for the Examination of Water and Wastewater (16th Edition)," American Public Health Association, 1985 and "Static Acute Bioassay Procedures for Hazardous Waste Samples," California Department of Fish and Game, Water Pollution Control Laboratory, revised November 1988" with fathead minnows (Pimephales promelas). The concentrations of the combined solution used in the $LC_{50}$ testing were 250 mg/L, 500 mg/L, and 750 mg/L. The mean survival percentage of the fathead minnows over 96 hours at the 250 mg/L and 500 mg/L concentrations was 100% and at the 750 mg/L concentration the mean survival percentage of the fathead minnows was 95%. The $LC_{50}$ of the combined solution was determined to be greater than 750 mg/L. Accordingly, the AERO-OPA™ was neutralized with only a single addition of neutralizer even though the basin would not hold the entire amount of AERO-OPA™ present in the reservoir.

Various aspects of the invention according to the present disclosure include, but are not limited to, the aspects listed in the following numbered clauses.

1. A method for in-basin neutralization in a chamber comprising a basin in fluid communication with a reservoir, the method comprising:
    adding neutralizer to the basin in excess of an amount of neutralizer suitable to neutralize a treatment solution in the reservoir;
    adding a first portion of the treatment solution to the basin;
    contacting, in the basin, the neutralizer with the first portion of the treatment solution to form a secondary solution and neutralizing the first portion of the treatment solution with the neutralizer;
    removing a first portion of the secondary solution from the basin wherein a second portion of the secondary solution remains in the basin;
    adding a second portion of the treatment solution to the basin; and
    contacting, in the basin, the second portion of the treatment solution with the second portion of the secondary solution to form a tertiary solution and neutralizing the second portion of the treatment solution with neutralizer in the second portion of the secondary solution.
2. The method of clause 1, wherein the basin has a first solution capacity and the reservoir has a second solution capacity larger than the first solution capacity.
3. The method of clauses 1-2, further comprising removing the tertiary solution from the basin.
4. The method of clause 3, further comprising rinsing at least one of the reservoir and the basin with an aqueous solution after removing the tertiary solution.
5. The method of clauses 1-4, further comprising removing a portion of the tertiary solution and adding a third portion of the treatment solution to the basin to form a quaternary solution.
6. The method of clauses 1-5, wherein the second portion of the secondary solution comprises an amount of neutralizer suitable to neutralize the second portion of the treatment solution.
7. The method of clauses 1-6, wherein neutralizing comprises forming an adduct between the treatment solution and the neutralizer.
8. The method of clauses 1-7, wherein the neutralizer is added to the basin in a mole ratio of active group in the neutralizer to active group in the treatment solution of greater than 1.3:1.
9. The method of clauses 1-8, wherein the neutralizer comprises at least one of an amino acid, ammonia, sodium hydroxide, hydrogen peroxide, sodium hypochlorite, and sodium bisulfate.
10. The method of clauses 1-9, wherein the treatment solution comprises at least one disinfectant selected from the group of an alcohol, an aldehyde, a quaternary ammonium compound, an oxidizer, and an antimicrobial metal solution.
11. The method of clauses 1-10, wherein the treatment solution comprises ortho-phthalaldehyde and the neutralizer comprises glycine.
12. The method of clauses 1-11, further comprising at least one of heating, agitating, and circulating at least one of the secondary solution and the tertiary solution.
13. The method of clauses 1-12, wherein the neutralizer is added to the basin once in order to neutralize the first and second portions of the treatment solution.
14. The method of clause 13, wherein remaining active treatment solution in the tertiary solution is less than 0.01% by weight of the tertiary solution.
15. A method for in-basin neutralization in a chamber comprising a basin in fluid communication with a reservoir, the basin has a first solution capacity and the reservoir has a second solution capacity larger than the first solution capacity, the method comprising:
    adding neutralizer to the basin in excess of an amount of neutralizer suitable to neutralize a disinfectant solution in the reservoir;
    adding a first portion of the disinfectant solution to the basin;
    contacting, in the basin, the neutralizer with the first portion of the disinfectant solution to form a secondary solution and neutralizing the first portion of the disinfectant solution with the neutralizer;
    removing a first portion of the secondary solution from the basin, wherein a second portion of the secondary solution remains in the basin, the second portion of the secondary solution comprises an amount of neutralizer suitable to neutralize a second portion of the disinfectant solution;
    adding the second portion of the disinfectant solution to the basin; and
    contacting the second portion of the disinfectant solution with the second portion of the secondary solution in the basin to form a tertiary solution and neutralizing the second portion of the disinfectant solution with neutralizer in the second portion of the secondary solution.
16. The method of clause 15, wherein the neutralizer is added to the basin once in order to neutralize the first and second portions of the disinfectant.
17. A system for in-basin neutralization comprising:
    a reservoir comprising a disinfectant solution;
    a basin in fluid communication with the reservoir, the basin suitable to receive disinfectant solution from the reservoir, the basin has a first solution capacity and the reservoir has a second solution capacity larger than the first solution capacity; and a neutralizing solution in the basin, the neutralizing solution suitable to neutralize the disinfectant solution in the reservoir, wherein a mole ratio of active group in the neutralizer to active group in the disinfectant solution is greater than 1.3:1.

18. The system of clause 17, wherein a mole ratio of neutralizer to active group in the disinfectant solution is greater than 1.5:1.

19. The system of clauses 17-18, wherein the neutralizer comprises at least one of an amino acid, ammonia, sodium hydroxide, hydrogen peroxide, sodium hypochlorite, and sodium bisulfite.

20. The system of clauses 17-19, wherein the disinfectant solution comprises at least one of an alcohol, an aldehyde, a quaternary ammonium compound, an oxidizer, and an antimicrobial metal solution.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

One skilled in the art will recognize that the herein described components, devices, operations/actions, and objects, and the discussion accompanying them, are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, operations/actions, and objects should not be taken limiting. While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A method for in-basin neutralization in a chamber comprising a basin in fluid communication with a reservoir, the method comprising:
   adding neutralizer to the basin in excess of an amount of neutralizer suitable to neutralize a treatment solution in the reservoir;
   adding a first portion of the treatment solution to the basin;
   contacting, in the basin, the neutralizer with the first portion of the treatment solution to form a secondary solution and neutralizing the first portion of the treatment solution with the neutralizer, wherein the neutralizing the first portion of the treatment solution with the neutralizer increases the $LC_{50}$ of the secondary solution to be greater than 500 mg/L;
   removing a first portion of the secondary solution from the basin wherein a second portion of the secondary solution remains in the basin;
   adding a second portion of the treatment solution to the basin; and contacting, in the basin, the second portion of the treatment solution with the second portion of the secondary solution to form a tertiary solution and neutralizing the second portion of the treatment solution with neutralizer in the second portion of the secondary solution.

2. The method of claim 1, wherein the basin has a first solution capacity and the reservoir has a second solution capacity larger than the first solution capacity.

3. The method of claim 1, further comprising removing the tertiary solution from the basin.

4. The method of claim 3, further comprising rinsing at least one of the reservoir and the basin with an aqueous solution after removing the tertiary solution.

5. The method of claim 1, further comprising removing a portion of the tertiary solution and adding a third portion of the treatment solution to the basin to form a quaternary solution.

6. The method of claim 1, wherein the second portion of the secondary solution comprises an amount of neutralizer suitable to neutralize the second portion of the treatment solution.

7. The method of claim 1, wherein neutralizing comprises forming an adduct between the treatment solution and the neutralizer.

8. The method of claim 1, wherein the neutralizer is added to the basin in a mole ratio of active group in the neutralizer to active group in the treatment solution of greater than 1.3:1.

9. The method of claim 1, wherein the neutralizer comprises at least one of an amino acid, ammonia, sodium hydroxide, hydrogen peroxide, sodium hypochlorite, and sodium bisulfate.

10. The method of claim 1, wherein the treatment solution comprises at least one disinfectant selected from the group of an alcohol, an aldehyde, a quaternary ammonium compound, an oxidizer, and an antimicrobial metal solution.

11. The method of claim 1, wherein the treatment solution comprises ortho-phthalaldehyde and the neutralizer comprises glycine.

12. The method of claim 1, further comprising at least one of heating, agitating, and circulating at least one of the secondary solution and the tertiary solution.

13. The method of claim 1, wherein the neutralizer is added to the basin once in order to neutralize the first and second portions of the treatment solution.

14. The method of claim 13, wherein remaining active treatment solution in the tertiary solution is less than 0.01% by weight of the tertiary solution after neutralizing the second portion of the treatment solution with neutralizer in the second portion of the secondary solution.

15. A method for in-basin neutralization in a chamber comprising a basin in fluid communication with a reservoir, the basin has a first solution capacity and the reservoir has a second solution capacity larger than the first solution capacity, the method comprising:
- adding neutralizer to the basin in excess of an amount of neutralizer suitable to neutralize a disinfectant solution in the reservoir;
- adding a first portion of the disinfectant solution to the basin;
- contacting, in the basin, the neutralizer with the first portion of the disinfectant solution to form a secondary solution and neutralizing the first portion of the disinfectant solution with the neutralizer, wherein the neutralizing the first portion of the disinfectant solution with the neutralizer increases the $LC_{50}$ of the secondary solution to be greater than 500 mg/L;
- removing a first portion of the secondary solution from the basin, wherein a second portion of the secondary solution remains in the basin, the second portion of the secondary solution comprises an amount of neutralizer suitable to neutralize a second portion of the disinfectant solution;
- adding the second portion of the disinfectant solution to the basin; and
- contacting the second portion of the disinfectant solution with the second portion of the secondary solution in the basin to form a tertiary solution and neutralizing the second portion of the disinfectant solution with neutralizer in the second portion of the secondary solution.

16. The method of claim 15, wherein the neutralizer is added to the basin once in order to neutralize the first and second portions of the disinfectant.

17. The method of claim 1, wherein the neutralizer comprises at least one of an amino acid, ammonia, sodium hydroxide, hydrogen peroxide, and sodium bisulfate.

18. The method of claim 1, wherein the treatment solution comprises an oxidizer and the neutralizer comprises sodium bisulfite.

19. A method for in-basin neutralization in a chamber comprising a basin in fluid communication with a reservoir, the method comprising:

- adding neutralizer to the basin in excess of an amount of neutralizer suitable to neutralize a treatment solution in the reservoir, wherein the neutralizer comprises sodium bisulfite;
- adding a first portion of the treatment solution to the basin, wherein the treatment solution comprises an oxidizer;
- contacting, in the basin, the neutralizer with the first portion of the treatment solution to form a secondary solution and neutralizing the first portion of the treatment solution with the neutralizer;
- removing a first portion of the secondary solution from the basin wherein a second portion of the secondary solution remains in the basin;
- adding a second portion of the treatment solution to the basin; and contacting, in the basin, the second portion of the treatment solution with the second portion of the secondary solution to form a tertiary solution and neutralizing the second portion of the treatment solution with neutralizer in the second portion of the secondary solution.

* * * * *